United States Patent [19]

Neumann

[11] Patent Number: 4,466,972
[45] Date of Patent: Aug. 21, 1984

[54] BENZOXADIAZOLES AND BENZOTHIADIAZOLES, THEIR PREPARATION AND PHARMACEUTICAL COMPOSITIONS CONTAINING THEM

[75] Inventor: Peter Neumann, Berne, Switzerland
[73] Assignee: Sandoz Ltd., Basel, Switzerland
[21] Appl. No.: 359,751
[22] Filed: Mar. 19, 1982

Related U.S. Application Data

[63] Continuation of Ser. No. 173,305, Jul. 29, 1980, abandoned, which is a continuation-in-part of Ser. No. 101,591, Dec. 10, 1979, abandoned, which is a continuation-in-part of Ser. No. 915,858, Jun. 15, 1978, abandoned.

[30] Foreign Application Priority Data

| Jun. 20, 1977 | [CH] | Switzerland | 7520/77 |
| Mar. 16, 1978 | [CH] | Switzerland | 2865/78 |
| Jun. 15, 1978 | [CH] | Switzerland | 5627/79 |
| Dec. 18, 1978 | [CH] | Switzerland | 12835/78 |
| Dec. 18, 1978 | [CH] | Switzerland | 12888/78 |
| Dec. 18, 1978 | [CH] | Switzerland | 12890/78 |
| Apr. 11, 1979 | [CH] | Switzerland | 3472/79 |
| Apr. 11, 1979 | [CH] | Switzerland | 3477/79 |
| Nov. 23, 1979 | [GB] | United Kingdom | 40624/79 |
| Dec. 8, 1979 | [DE] | Fed. Rep. of Germany | 294945 |

[51] Int. Cl.³ .................. C07D 513/00; A61K 31/44
[52] U.S. Cl. .................. 424/266; 546/271; 544/80; 424/248.51
[58] Field of Search .................. 424/266; 546/271

[56] References Cited

U.S. PATENT DOCUMENTS

| 3,883,543 | 5/1975 | Bossert | 546/321 |
| 3,932,646 | 1/1976 | Meyer | 424/266 |
| 3,946,026 | 3/1976 | Meyer et al. | 546/321 |
| 3,946,027 | 3/1976 | Bossert et al. | 546/321 |
| 3,951,988 | 4/1976 | Meyer et al. | 546/112 |
| 4,017,629 | 4/1977 | Habicht et al. | 424/266 |
| 4,145,432 | 3/1979 | Sato | 424/266 |

FOREIGN PATENT DOCUMENTS

| 0750139 | 11/1970 | Belgium | 546/321 |
| 2210667 | 9/1973 | Fed. Rep. of Germany | 546/321 |
| 2210672 | 9/1973 | Fed. Rep. of Germany | 546/321 |
| 1425059 | 2/1976 | United Kingdom | 424/266 |

*Primary Examiner*—Alan L. Rotman
*Attorney, Agent, or Firm*—Gerald D. Sharkin; Robert S. Honor; Joseph J. Borovian

[57] ABSTRACT

Compounds of formula I,

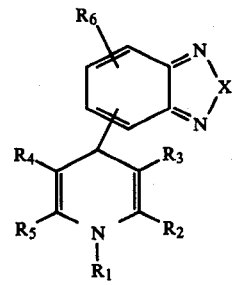

wherein X is oxygen or sulphur, and $R_1$–$R_6$ are various substituents.

The compounds are useful for treating coronary insufficiency, intermittent claudication, cerebrovascular insults, spasms in muscles and hypertension.

34 Claims, No Drawings

BENZOXADIAZOLES AND BENZOTHIADIAZOLES, THEIR PREPARATION AND PHARMACEUTICAL COMPOSITIONS CONTAINING THEM

This is a continuation of application Ser. No. 173,305 filed July 29, 1980 which in turn is a continuation-in-part of Ser. No. 101,591 filed Dec. 10, 1979, which in turn is a continuation-in-part of Ser. No. 915,858, filed June 15, 1978, all now abandoned.

The present invention relates to benzoxadiazoles and benzothiadiazoles having a 4-dihydropyridine moiety.

The present invention provides in particular compounds of formula I,

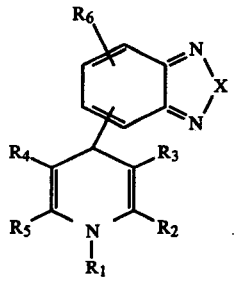

wherein $R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl ($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, COR$_7$, COOR$_7$, S(O)$_n$R$_7$

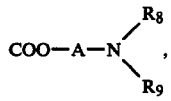

wherein n is 0, 1 or 2, $R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl ($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), di[alkyl($C_{1-4}$)]aminoalkyl, phenyl, phenylalkyl($C_{7-10}$), a 5- or 6-membered heterocyclic ring containing one heteroatom selected from nitrogen, oxygen or sulphur and may contain additionally 1, 2 or 3 ring nitrogen atoms, or alkyl($C_{1-4}$) substituted by a 5- or 6-membered heterocyclic ring containing one heteroatom selected from nitrogen, oxygen or sulphur and may contain additionally 1, 2 or 3 ring nitrogen atoms, is alkylene($C_{1-6}$), $R_8$ and $R_9$, independently, are alkyl($C_{1-6}$), alkenyl or alkinyl($C_{3-6}$), cycloalkyl($C_{3-7}$), cycloalkylalkyl ($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), di[alkyl($C_{1-4}$)]aminoalkyl, phenyl, phenylalkyl($C_{7-10}$), or $R_8$ and $R_9$ together with the nitrogen atom form a 5-, 6-, or 7-membered heterocyclic ring, which may contain a further heteromember selected from oxygen, sulphur and a group =N—R$_{10}$, wherein R$_{10}$ is alkyl ($C_{1-4}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)amino, di[alkyl($C_{1-4}$)]amino, alkanoyl($C_{1-5}$)amino, carbalkoxy($C_{2-5}$), aminocarbonyl, trifluoromethoxy, cyano, sulfamyl, alkyl($C_{1-4}$)sulfamyl or di[alkyl ($C_{1-4}$)]sulfamyl, and X is oxygen or sulphur. One group of compounds comprises compounds of formula I as defined above, with the proviso that, when $R_1$ is hydrogen, alkyl($C_{1-6}$), alkenyl($C_{3-6}$), alkinyl ($C_{3-6}$), cycloalkyl($C_{3-7}$), cycloalkylalkyl($C_{4-8}$), phenylalkyl($C_{7-9}$) or phenylalkenyl($C_{9-12}$), the phenylring being unsubstituted or mono-, di- or trisubstituted independently by halogen, hydroxy, alkyl($C_{1-4}$) or alkoxy($C_{1-4}$), $R_2$ and $R_5$, independently, are hydrogen or alkyl($C_{1-6}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and X is oxygen or sulphur, then at least one of the substituents R$_3$ and R$_4$ is other than COR$_7^I$, wherein R$_7^I$ is alkyl($C_{1-6}$), alkenyl($C_{3-6}$), alkinyl($C_{3-6}$), cycloalkyl($C_{3-7}$), cycloalkylalkyl($C_{4-8}$), and is other than COOR$_7^{II}$, wherein R$_7^{II}$ is alkyl($C_{1-6}$), alkenyl ($C_{3-6}$), alkinyl($C_{3-6}$),cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl($C_{4-8}$).

In any of the above radicals alkyl of 1 to 6 carbon atoms is preferably of 1 to 4 carbon atoms, especially of 1 to 2 carbon atoms. Any alkyl, alkoxy, alkylthio or alkylsulfonyl radical of 1 to 4 carbon atoms is preferably of 1 to 2 carbon atoms. The hydroxy, alkoxy, hydroxyalkoxy, amino or alkylamino group of the hydroxyalkyl, alkoxyalkyl, hydroxyalkoxyalkyl, aminoalkyl or alkylaminoalkyl moiety in COOR$_7$ is preferably not attached to the α-carbon atom and is preferably attached to the distal terminal carbon atom. Any hydroxyalkyl, alkoxyalkyl, hydroxyalkoxyalkyl, aminoalkyl or alkylaminoalkyl radical preferably has an ethylene or propylene moiety substituted by hydroxy, alkoxy, hydroxyalkoxy, amino or alkylamino respectively. The alkyl moiety of cycloalkylalkyl is conveniently methyl. Halogen means fluorine, chlorine or bromine and is especially chlorine. Cycloalkyl or the cycloalkyl moiety of cycloalkylalkyl is conveniently cyclopropyl or cyclopentyl or cyclohexyl. The multiple bond of alkenyl, alkinyl or phenylalkenyl in R$_1$ or COOR$_7$ is preferably not in the α, β position. Alkenyl or alkinyl preferably has 3 to 5 carbon atoms. Alkenyl is conveniently allyl or 2-methylallyl. Alkinyl is conveniently propinyl. Phenylalkenyl preferably has the trans-configuration and is for example cinnamyl. When R$_1$ is optionally substituted phenylalkyl, the phenyl group is preferably unsubstituted. When the phenyl group is di- or tri-substituted, preferably the substituents are the same.

When R$_7$ is alkyl, this is preferably branched. When R$_7$ contains a heterocyclic ring this may be for example furyl, thienyl, pyrrolyl, thiazolyl, isothiazolyl, thiadiazolyl, oxazolyl, isoxazolyl, oxadiazolyl, imidazolyl, pyrazolyl, triazolyl, tetrazolyl, pyridyl, pyrimidinyl, pyrazinyl, pyridazinyl, piperidinyl, morpholinyl or triazinyl.

When $R_8$ and $R_9$ together with the nitrogen atom to which they are bound, form a heterocyclic ring, this is preferably saturated and may be for example pyrrolidine, piperidine, piperazine, N-alkylpiperazine, morpholine, azepane, diazepane or N-alkyl-diazepane.

$R_1$ is conveniently hydrogen. $R_2$ is conveniently identical to $R_5$. $R_2$ is conveniently alkyl. $R_3$ and/or $R_4$ is conveniently $COOR_7$ or

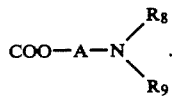

$R_7$ is conveniently alkyl, preferably branched or alkoxyalkyl, where the alkoxy moiety is preferably branced. A is conveniently ethylene. $R_8$ and $R_9$ are conveniently alkyl or phenylalkyl.

The present invention also provides a process for the production of a compound of formula I as defined above, comprising replacing the moiety —HC=Y in a compound of formula II,

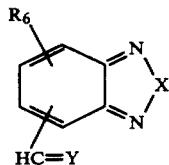

wherein
$R_6$ and X are as defined above, and
—HC=Y is
(i) formyl,
(ii) a radical of formula

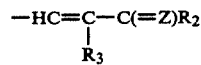

or
(iii) a radical of formula

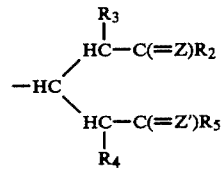

wherein
Z and Z' are independently oxygen or $NR_1$, and $R_1$ to $R_5$ are as defined above,
by a moiety of formula III,

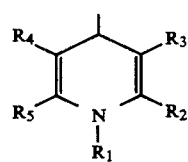

wherein $R_1$ to $R_5$ are as defined above.

The process may be effected in conventional manner for analogous dihydropyridine syntheses, e.g. according to Hantzsch. When the moiety —HC=Y is formyl and when it is desired to produce a compound of formula I, wherein $R_2$ is identical to $R_5$ and $R_3$ is identical to $R_4$, it is convenient to react a compound of formula II with a compound of formula IV, $$R_5CO-CH_2-R_4 \qquad IV$$

wherein $R_4$ and $R_5$ are as defined above, in the presence of a compound of formula V, $$H_2NR_1 \qquad V$$

wherein $R_1$ is as defined above.

Preferably at least 2 moles of a compound of formula IV per mole of a compound of formula II are present. Alternatively a compound of formula II may be reacted with a compound of formula VI, $$R_5-C(NH-R_1)=CH-R_4 \qquad VI$$

wherein $R_1$, $R_4$ and $R_5$ are as defined above.

Preferably at least 2 moles of a compound of formula VI per mole of a compound of formula II are present. Preferably also $R_1$ is hydrogen.

When the moiety —HC=Y is formyl and preferably when it is desired to produce a compound of formula I wherein $R_2$ is different to $R_5$ and/or $R_3$ is different to $R_4$, it is also possible to react such a compound of formula II with a compound of formula IV and a compound of formula VII, $$R_2-C(NH-R_1)=CH-R_3 \qquad VII$$

wherein $R_2$, $R_1$ and $R_3$ are as defined above.

It will be appreciated that a compound of formula VI may be formed as an intermediate during the reaction of a compound of formula IV and a compound of formula V. A compound of formula II, wherein —HC=Y is a radical (ii) or (iii), may be formed as an intermediate in the above reactions. They may however be produced by different processes.

Alternatively or particularly for the production of a compound of formula I, wherein $R_2$ is different to $R_5$ and/or $R_3$ is different to $R_4$, it is convenient to react a compound of formula II, wherein the moiety —HC=Y is a radical (ii) with a compound of formula IV or VI, and where appropriate, with a compound of formula V. A compound of formula II, wherein the moiety —HC=Y is a radical (iii) may be an intermediate.

In the above reactions it is possible in certain instances when $R_2$, $R_3$, $R_4$ and $R_5$ are not identical that more than one isomer of formula I may be formed. If so these may be separated in conventional manner, e.g. by column or thin layer chromatography.

When the starting material is a compound of formula II, wherein —HC=Y is a radical iii), the reaction is a ring cyclisation. When Z and Z' are both oxygen, then an amine of formula V should be present.

However, all the above reactions may be effected under the same conditions.

The reaction may be effected conveniently in solution. A suitable solvent is water, ethanol, dioxane, dimethyl formamide, dimethyl sulphoxide, pyridine or glacial acetic acid. Suitable reaction temperatures may be from 20° to 160° C., preferably from 60° to 120° C.

Insofar as the production of starting materials is not particularly described these compounds are known or may be produced in analoqous manner to known compounds.

The basic compounds for formula I may be converted into acid addition salt forms in conventional manner and vice versa. Suitable acids are e.g. maleic acid, oxalic acid, methanesulphonic acid, hydrochloric acid and hydrobromic acid.

The present invention provides a group of compounds of formula Ia,

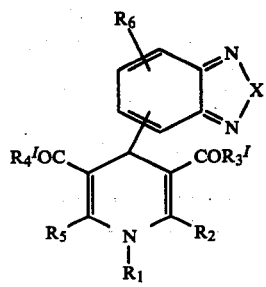

Ia wherein $R_1$ is hydrogen, alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, phenylalkyl of 7 to 9 carbon atoms or phenylalkenyl of 9 to 12 carbon atoms, the phenyl ring being unsubstituted or mono-, di- or trisubstituted independently by halogen, hydroxy or alkyl or alkoxy of 1 to 4 carbon atoms, $R_2$ and $R_5$, independently, are hydrogen or alkyl of 1 to 6 carbon atoms, $R_3{}^I$ and $R_4{}^I$, independently, are alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, alkoxy of 1 to 6 carbon atoms, hydroxyalkoxy of 2 to 6 carbon atoms, alkoxyalkoxy of 3 to 6 carbon atoms, hydroxyalkoxyalkoxy of 4 to 8 carbon atoms, alkenyloxy or alkinyloxy of 3 to 6 carbon atoms, cycloalkyloxy of 3 and 7 carbon atoms or cycloalkylalkoxy of 4 to 8 carbon atoms, $R_6$ is hydrogen, halogen, alkyl or alkoxy or alkylthio or alkylsulfonyl, each of 1 to 4 carbon atoms, trifluoromethyl, nitro or hydroxy, and X is oxygen or sulphur.

In any of the above radicals alkyl of 1 to 6 carbon atoms is preferably of 1 to 4 carbon atoms, especially of 1 or 2 carbon atoms. Any alkyl, alkoxy, alkylthio or alkylsulfonyl radical of 1 to 4 carbon atoms is preferably of 1 or 2 carbon atoms. The alkyl moiety of cycloalkylalkyl or cycloalkylalkoxy is conveniently methyl. Halogen means fluorine, chlorine or bromine and is especially chlorine. Cycloalkyl or the cycloalkyl moiety of cycloalkylalkyl or cycloalkylalkoxy is conveniently cyclopropyl or cyclopentyl or cyclohexyl. The multiple bond of alkenyl, alkinyl, alkenyloxy, alkinyloxy or phenylalkenyl is preferably not in the α, βposition. Alkenyl, alkenyloxy, alkinyl or alkinyloxy preferably has 3 to 5 carbon atoms. Alkenyl or the alkenyl moiety of alkenyloxy is conveniently allyl or 2-methylallyl. Alkinyl or the alkinyl moiety of alkinyloxy is conveniently propinyl. Phenylalkenyl preferably has the trans-configuration and is for example cinnamyl. When $R_1$ is optionally substituted phenyllalkyl, the phenyl group is preferably unsubstituted. When the phenyl group is di- or tri-substituted, preferably the substituents are the same. When $R_3{}^I$ and/or $R_4{}^I$ is alkoxy, this is preferably ethoxy or methoxy. When $R_3{}^I$ and/or $R_4{}^I$ is alkoxy-alkoxy or hydroxyalkoxyalkoxy, preferably the carbon chain between the two ether oxygen atoms is of 2 carbon atoms. The hydroxy group of hydroxyalkoxy or of hydroxyalkoxyalkoxy is preferably not attached to the carbon atom attached to an ether oxygen atom. $R_1$ is preferably hydrogen. $R_2$ is conveniently identical to $R_5$. $R_2$ and/or $R_5$ is preferably methyl. $R_3{}^I$ and/or $R_4{}^I$ is preferably alkoxy or alkoxyalkoxy, especially n-butyloxyothoxy. $R_6$ is conveniently halogen, alkyl or alkoxy, or especially hydrogen. $R_6$ is conveniently adjacent to the dihydropyridine moiety which in turn is conveniently in the 4-position.

In the following examples all temperatures are in degrees Centrigrade and are uncorrected.

Example 1:
4-(2,1,3-Benzoxadiazol-4-yl)-2,6-dimethyl-1,4-dihydropyridine-3,5-dicarboxylic acid diethyl ester 3.2 g of 2,1,3-benzoxadiazole-4-aldehyde, 5.7 g of acetoacetic acid ethyl ester, 2.5 ml of concentrated ammonia and 10 ml of ethanol are refluxed for 6 hours. The mixture is subsequently evaporated and the residual oil is chromatographed on silica gel with chloroform/acetic acid ethyl ester (9:1) to yield the title compound. The product is recrystallised from toluene, m.p. 153°-155°.

By using the process described in Example 1, and corresponding starting compounds, e.g. a compound of formula II, wherein —HC=Y is a radical (i) and compounds of formula IV and V, and for Examples 18 and 19 a compound of formula II, wherein —HC=Y is a radical (ii), wherein Z is oxygen and a compound of formula VI, the following compounds of formula Ia may be obtained, wherein y indicates the position of the dihydropyridine moiety:

| Example | $R_1$ | $R_2$ | $R_3{}^I$ | $R_4{}^I$ | $R_5$ | $R_6$ | X | y | m.p. |
|---|---|---|---|---|---|---|---|---|---|
| 2 | H | CH$_3$ | OC$_2$H$_5$ | OC$_2$H$_5$ | CH$_3$ | H | S | 4 | 146–148 |
| 3 | H | CH$_3$ | OC(CH$_3$)$_3$ | OC(CH$_3$)$_3$ | CH$_3$ | H | S | 4 | 193–199 |
| 4 | H | CH$_3$ | OCH$_3$ | OCH$_3$ | CH$_3$ | 7-Cl | O | 4 | 207–211 |
| 5 | H | CH$_3$ | OCH$_3$ | OCH$_3$ | CH$_3$ | H | S | 4 | 215–216 |
| 6 | H | CH$_3$ | OC$_2$H$_5$ | OC$_2$H$_5$ | CH$_3$ | 5-OCH$_3$ | S | 4 | 201–203 |
| 7 | H | CH$_3$ | OC$_2$H$_5$ | OC$_2$H$_5$ | CH$_3$ | 7-Cl | S | 4 | 135–155 |
| 8 | H | CH$_3$ | OC$_2$H$_5$ | OC$_2$H$_5$ | CH$_3$ | H | S | 5 | 152–153 |
| 9 | H | CH$_3$ | OC$_2$H$_5$ | OC$_2$H$_5$ | CH$_3$ | 4-Cl | S | 5 | 198–200 |
| 10 | H | CH$_3$ | C(CH$_3$)$_3$ | C(CH$_3$)$_3$ | CH$_3$ | H | S | 4 | |
| 11 | H | CH$_3$ | CH$_3$ | CH$_3$ | CH$_3$ | 7-Cl | O | 4 | |
| 12 | H | CH$_3$ | CH$_3$ | CH$_3$ | CH$_3$ | H | S | 4 | 225–228 |
| 13 | H | CH$_3$ | C$_2$H$_5$ | C$_2$H$_5$ | CH$_3$ | 5-OCH$_3$ | S | 4 | |
| 14 | H | CH$_3$ | C$_2$H$_5$ | C$_2$H$_5$ | CH$_3$ | 7-Cl | S | 4 | |
| 15 | H | CH$_3$ | C$_2$H$_5$ | C$_2$H$_5$ | CH$_3$ | H | S | 5 | |
| 16 | H | CH$_3$ | C$_2$H$_5$ | C$_2$H$_5$ | CH$_3$ | 4-Cl | S | 5 | |
| 17 | H | CH$_3$ | CH$_3$ | CH$_3$ | CH$_3$ | H | O | 4 | 218–222 |

| Example | $R_1$ | $R_2$ | $R_3^I$ | $R_4^I$ | $R_5$ | $R_6$ | X | y | m.p. |
|---|---|---|---|---|---|---|---|---|---|
| 18 | H | $CH_3$ | $CH_3$ | $OC_2H_5$ | $CH_3$ | H | O | 4 | 186–188 |
| 19 | H | $CH_3$ | $CH_3$ | $OC_2H_5$ | $CH_3$ | H | S | 4 | 146–148 |

Example 20:
4-(2,1,3-Benzoxadiazol-4-yl)-2,6-dimethyl-1,4-dihydro-3-methoxy carbonyl-pyridine-5-carboxylic acid isobutyl ester 3 g of 2,1,3-benzoxadiazole-b 4-aldehyde, 3.2 g of acetoacetic acid isobutyl ester, 2.3 g β-aminocrotonic acid methyl ester and 10 ml of ethanol are stirred under reflux for 3 hours. The mixture is subsequently evaporated and the residue is chromatographed on silica gel with chloroform/acetic acid ethyl ester (8:1) to yield the title compound. The product is recrystallised from diisopropyl ether and methylcyclohexane, m.p. 148°–158°.

By using the process described in Example 1, and corresponding starting compounds, e.g. a compound of formula II, wherein —HC=Y is a radical (i) and compounds of formula IV and V, and for Examples 23, 24 and 27 to 36 a compound fo formula II, wherein —HC=Y is a radical (ii), wherein Z is oxygen and a compound of formula VI, the following compounds of formula Ia, wherein $R_2$ and $R_5$ are each methyl and $R_6$ is hydrogen, may be obtained, wherein y indicates the position of the dihydropyridine moiety:

| Comp. | $R_3^I$ | $R_4^I$ | $R_1$ | y | x | m.p. |
|---|---|---|---|---|---|---|
| 21 | $OCH_3$ | $OCH_3$ | H | 4 | O | 215–221 |
| 22 | $OC_2H_5$ | $OC_2H_5$ | H | 5 | O | 173–174 |
| 23 | $OCH_2CH(CH_3)_2$ | $OC_2H_5$ | H | 4 | S | 85–95 |
| 24 | $OCH_2CH(CH_3)_2$ | $OC_2H_5$ | H | 4 | O | 145–146.5 |
| 25 | $OC(CH_3)_3$ | $OC(CH_3)_3$ | H | 4 | O | 207–210 |
| 26 | $OCH_2CH(CH_3)_2$ | $OCH_2CH(CH_3)_2$ | H | 4 | O | 135.5–137 |
| 27 | $O(CH_2)_2OC_2H_5$ | $OC_2H_5$ | H | 4 | O | 126–128 |
| 28 | $O(CH_2)_2OC_2H_5$ | $OC_2H_5$ | H | 4 | S | oil |
| 29 | $O(CH_2)_2OC_2H_5$ | $OC_2H_5$ | H | 5 | S | 72–78 |
| 30 | $OCH(CH_3)_2$ | $OCH_3$ | H | 4 | O | 168–170 |
| 31 | $O(CH_2)_2OCH_3$ | $OCH_3$ | H | 4 | O | 151–153 |
| 32 | $O(CH_2)_2OCH(CH_3)_2$ | $OCH_3$ | H | 4 | O | 114–120 |
| 33 | $O(CH_2)_2OC_2H_5$ | $OCH_3$ | H | 4 | O | 140–147 |
| 34 |  | $OCH_3$ | H | 4 | O | 156–163 |
| 35 | $O(CH_2)_2OCH_3$ | $OCH(CH_3)_2$ | H | 4 | O | 119 |
| 36 | $OCH_3$ | $OC_2H_5$ | H | 4 | O | 159 |
| 37 | $OC_2H_5$ | $OC_2H_5$ | $CH_3$ | 4 | O | 106 |
| 38 | $OC_2H_5$ | $OC_2H_5$ | $n\text{-}C_3H_7$ | 4 | O | 99 |

In addition from a compound of formula II, wherein —HC=Y is a radical (ii), wherein Z is oxygen and a compound for formula VI there may be made the following compounds of formula I, wherein y indicates the position of the dihydropyridine moiety:

| Ex. | $R_1$ | $R_2$ | $R_3$ | $R_4$ | $R_5$ | $R_6$ | X | y | m.p. |
|---|---|---|---|---|---|---|---|---|---|
| 39 | H | $CH_3$ | CN | COO—i-Bu | $CH_3$ | H | O | 4 | 123–124.5 |
| 40 | H | $CH_3$ | $COOC_2H_5$ | $SO_2CH_3$ | $CH_3$ | H | O | 4 | 204–205 |
| 41 | H | $CH_3$ | CN | $COOC_2H_5$ | $CH_3$ | H | O | 4 | 167–177 |
| 42 | H | $CH_3$ | CN | $COOC_2H_5$ | $CH_3$ | H | S | 4 | 187–190 |
| 43 | H | $CH_3$ | CN | $COOCH_2CH(CH_3)_2$ | $CH_3$ | H | S | 4 | 166–171 |
| 44 | H | $CH_3$ | $COOCH_3$ | $COC_6H_5$ | $CH_3$ | H | O | 4 | 192–201 |
| 45 | H | $CH_3$ | $COO(CH_2)_2N(CH_3)(CH_2C_6H_5)$ | $COOC_2H_5$ | $CH_3$ | H | O | 4 | 180–184** |
| 46 | H | $CH_3$ | $COO(CH_2)_2N(CH_3)(CH_2C_6H_5)$ | $COOC_2H_5$ | $CH_3$ | H | S | 4 | 173–175** |
| 47 | H | $CH_3$ | $COO(CH_2)_2N(CH_3)_2$ | $COO(CH_2)_2N(CH_3)_2$ | $CH_3$ | H | O | 4 | 188–191* fumarate |
| 48 | H | $CH_3$ | $COO(CH_2)_2N(CH_3)_2$ | $COO(CH_2)_2N(CH_3)_2$ | $CH_3$ | H | S | 4 | 156–159 fumarate |
| 49 | H | $CH_3$ | $COO(CH_2)_2N(CH_3)_2$ | $COOC_2H_5$ | $CH_3$ | H | O | 4 | |
| 50 | H | $CH_3$ | $COO(CH_2)_2N(CH_3)_2$ | $COOC_2H_5$ | $CH_3$ | H | S | 4 | 166–176 hydrogenfumarate |
| 51 | H | $CH_3$ | $COO(CH_2)_2N(CH_3)(CH_2C_6H_5)$ | $COOC_2H_5$ | $CH_3$ | H | S | 5 | oil |

-continued

| Ex. | R$_1$ | R$_2$ | R$_3$ | R$_4$ | R$_5$ | R$_6$ | X | y | m.p. |
|---|---|---|---|---|---|---|---|---|---|
| 52 | H | CH$_3$ | COO(CH$_2$)$_2$N(CH$_3$)(CH$_2$C$_6$H$_5$) | COOC$_2$H$_5$ | CH$_3$ | H | O | 5 | oil |
| 53 | H | CH$_3$ | COO(CH$_2$)$_2$N(CH$_3$)(CH$_2$C$_6$H$_5$) | COOCH$_3$ | CH$_3$ | H | O | 4 | 182–195** |
| 54 | H | Δ | COOC$_2$H$_5$ | COOC$_2$H$_5$ | CH$_3$ | H | O | 4 | 97–99 |
| 55 | H | Δ | COOCH$_3$ | COOCH$_3$ | CH$_3$ | H | O | 4 | 160–163 |
| 56 | H | Δ | COOCH$_3$ | COOCH$_3$ | Δ | H | O | 4 | 118–120 |
| 57 | H | Δ | COOC$_2$H$_5$ | COOC$_2$H$_5$ | Δ | H | O | 4 | 110–112 |
| 58 | H | CH$_3$ | COO(CH$_2$)$_2$—C$_6$H$_5$ | COOCH$_3$ | CH$_3$ | H | O | 4 | 156 |
| 59 | H | CH$_3$ | COOCH$_3$ | COOCH$_2$C$_6$H$_5$ | CH$_3$ | H | O | 4 | 131–136 |

\* decomposition
\*\* hydrochloride

In addition from a compound of formula II, wherein —HC═Y is a radical (ii), wherein Z is oxygen and a compound of formula VI there may be made the following compounds of formula Ia wherein X═S and the 1,4-dihydropyridine moiety is in the 5-position and R$_1$ to R$_6$ are respectively:

(a) CH$_3$; H; nC$_6$H$_{13}$; nC$_6$H$_{13}$; H; 4-C$_2$H$_5$; or (b) nC$_6$H$_{13}$; nC$_6$H$_{13}$; C$_2$H$_5$.CH═CH.CH$_2$; C$_2$H$_5$.CH═CH.CH$_2$; nC$_6$H$_{13}$; 6-C$_2$H$_5$S; or (c) C$_2$H$_5$.CH═CH.CH$_2$; H; ▷—; ▷—H; 7-CF$_3$; or (d) ▷—; H; ⬡—; ⬡—; H; 4-NO$_2$; or (e) ⬡—; H; C$_2$H$_5$O.CH$_2$O; C$_2$H$_5$O.CH$_2$O; H; 4-OH; or (f) C$_6$H$_5$—CH$_2$; H; CH$_2$.O.C$_2$H$_4$.O(OH); CH$_2$.O.C$_2$H$_4$O(OH); H; H; or (g) 3-Cl-C$_6$H$_4$—[CH$_2$]$_3$; H; C$_2$H$_5$.CH═CH.CH$_2$O; C$_2$H$_5$.CH═CH.CH$_2$O; H; H; or (h) (2-C$_2$H$_5$, 4-C$_2$H$_5$O-C$_6$H$_3$)—[CH$_2$]$_3$; H; ⬡—O; ⬡—O; H; H; or (i) (4-Br, 2-F, 3-Cl-C$_6$H$_2$)—[CH$_2$]$_3$; H; ▷—O; ▷—O; H; H;

(j) (3-OH-C$_6$H$_4$)—CH═CH—CH$_2$; H, HO(CH$_2$)$_4$O—; HO(CH$_2$)$_4$O—; H; C$_2$H$_5$SO$_2$; or (k) C$_2$H$_5$—C≡C—CH$_2$; H; ▷—; ▷—; H; 7-CF$_3$; or (l) nC$_6$H$_{13}$; nC$_6$H$_{13}$; CH≡C—CH$_2$; CH≡C—CH$_2$; nC$_6$H$_{13}$; 6-C$_2$H$_5$S; or (m) (3-Cl-C$_6$H$_4$)—[CH$_2$]$_3$; H; C$_2$H$_5$—C≡C—CH$_2$O; H; H; or (n) ▷—CH$_2$; H; ⬡—CH$_2$; ⬡—CH$_2$; H; 4-NO$_2$; or

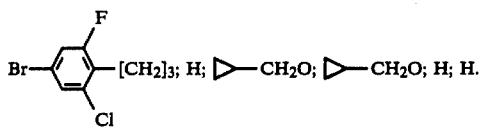

(o) Br—[aryl with F, Cl]—[CH₂]₃; H; ▷—CH₂O; ▷—CH₂O; H; H.

| | R₁ | R₂ | R₃ | R₄ | R₅ | R₆ | y | X |
|---|---|---|---|---|---|---|---|---|
| (p) | $C_4H_8C{\equiv}CH$ | $CH_3$ | CO—▷ | $COOCH_2C{\equiv}CH$ | $CH_3$ | 7-$OCF_3$ | 5 | S |
| (q) | $C{\equiv}C-C_2H_5$ | H | $COOCH_2$—◁   $COOC_3H_6$—⬡ | | $C_2H_5$ | 6-CN | 4 | S |
| (r) | $CH(C_6H_5)CH_3$ | $CH_2$—▷ | $SOC_2H_4OC_2H_5$ | $COCH_2-CH{=}CH_2$ | $CH_2$—▷ | 7-$nC_4H_9$ | 4 | O |
| (s) | $C_4H_9$—▷ | $C_2H_5$ | CN | $CO(CH_2)_2N(C_3H_7)_2$ | $C_2H_5$ | 6-Br | 5 | S |
| (t) | $C_5H_{10}$—◁ | $C_2H_5$ | CN | $COOCH_2-C{\equiv}CH$ | $CH_3$ | 6-Br | 5 | S |

By using the process described in Example 1, and corresponding starting compounds, e.g. a compound of formula II, wherein —HC=Y is a radical (i) and compounds of formula IV and V, and for Examples 61, 62 and 65 to 74 a compound of formula II, wherein —HC=Y is a radical (ii), wherein Z is oxygen and a compound of formula VI, the following compounds of formula I, wherein $R_2$ and $R_5$ are each methyl and $R_6$ is hydrogen, may be obtained, wherein y indicates the position of the dihydropyridine moiety and $R_3$ and $R_4$ are $COR_7^I$ and $COR_7^{II}$ respectively:

| Comp. | $R_7^I$ | $R_7^{II}$ | $R_1$ | y | X |
|---|---|---|---|---|---|
| 60 | $C_2H_5$ | $C_2H_5$ | H | 5 | O |
| 61 | $CH_2CH(CH_3)_2$ | $C_2H_5$ | H | 4 | S |
| 62 | $CH_2CH(CH_3)_2$ | $C_2H_5$ | H | 4 | O |
| 63 | $C(CH_3)_3$ | $C(CH_3)_3$ | H | 4 | O |
| 64 | $CH_2CH(CH_3)_2$ | $CH_2CH(CH_3)_2$ | H | 4 | O |
| 65 | $(CH_2)_2OC_2H_5$ | $C_2H_5$ | H | 4 | O |
| 66 | $(CH_2)_2OC_2H_5$ | $C_2H_5$ | H | 4 | S |
| 67 | $(CH_2)_2OC_2H_5$ | $C_2H_5$ | H | 5 | S |
| 68 | $CH(CH_3)_2$ | $CH_3$ | H | 4 | O |
| 69 | $(CH_2)_2OCH_3$ | $CH_3$ | H | 4 | O |
| 70 | $(CH_2)_2OCH(CH_3)_2$ | $CH_3$ | H | 4 | O |
| 71 | $(CH_2)_2OC_2H_5$ | $CH_3$ | H | 4 | O |
| 72 | cyclopentyl | $CH_3$ | H | 4 | O |
| 73 | $(CH_2)_2OCH_3$ | $CH(CH_3)_2$ | H | 4 | O |
| 74 | $CH_3$ | $C_2H_5$ | H | 4 | O |
| 75 | $C_2H_5$ | $C_2H_5$ | $CH_3$ | 4 | O |
| 76 | $C_2H_5$ | $C_2H_5$ | $n-C_3H_7$ | 4 | O |

The compounds of formula I exhibit pharmacological activity. In particular, they lead to a dilation of the coronary vessels as demonstrated by the results of tests measuring the blood flow to the myocardium of an anaesthetised cat by means of the microsphere method (Rudolph A. M. and Heymann M. S.: Circulation Research 21, 163, 1967) upon administration of from 30 to 50 μg/kg i.v. or of from 50 to 150 μg/kg i.d. of the active substance.

The compounds of formula I also possess a favourable effect against angina pectoris, as shown by the increase of the coronary flow of an anesthetised cat upon administration of the active substance.

The compounds of formula I are useful in the treatment of coronary insufficiency. For the abovementioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form, For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I increase the blood flow to limbs, e.g. leg musculature, as can be shown by means of the microsphere method on the anaesthetised cat upon administration of from 30 to 50 μg/kg i.v. or from 50 to 150 μg/kg i.d. of the compounds.

The compounds of formula I are therefore useful for treatment of intermittent claudication and other peripheral disturbances of blood flow to limb muscles. For the above-mentioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I increase cerebral blood flow, as can be shown by means of the microsphere method on the anesthetised cat upon administration of from 30 to 50 μg/kg i.v. or 50 to 150 μg/kg i.d. of the compounds.

The compounds of formula I are therefore useful in the treatment of cerebrovascular insults (accidents). For the above-mentioned use the dosage will, of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

The compounds of formula I possess calciumantagonistic activity, as indicated in standard tests, for example by an inhibition of a calcium induced contraction of isolated dog coronary arteries suspended in a depolarizing solution at concentration of $10^{-10}$ to $10^{-8}$ M of the compounds according to the principles of Godfraind and Kaba, Brit. J. Pharm. 36, 549–560, 1969. The compounds are therefore useful as spasmolytic agents, for the treatment of spasms in muscles. For the above-mentioned use the dosage will of course, vary depending on the compound employed, mode of administration and therapy desired. However, in general satisfactory results are obtained with a daily dosage of 0.01 to 10 mg/kg animal body weight, conveniently given in divided doses 2 to 4 times a day or in sustained release form. For the larger mammal, the total daily dosage is in the range from about 5 to 100 mg, and dosage forms suitable for oral administration comprise from about 1.25 mg to about 50 mg of the compounds admixed with a solid or a liquid pharmaceutical carrier or diluent.

Additionally, the compounds of formula I exhibit antihypertensive activity, as indicated by a blood pressure lowering activity in standard tests.

For example, the compounds exhibit a blood pressure lowering effect in the Grollman rat test [see A. Grollman, Proc. Soc. Expt. Biol. and Med. 57, 104 (1944)] on s.c. administration of from 0.1 to 10 mg/kg animal body weight of the compounds.

The compounds are therefore useful as anti-hypertensive agents. For this use the dosage will, of course, vary depending on the compound employed, mode of administration and therapy desired. However, in general, satisfactory results are obtained with a daily dosage of from 0.5 to 50 mg/kg animal body weight, conveniently given in divided doses 2 to 4 times a day or in sustained release form. For the larger mammal, the total daily dosage is in the range form about 5 to about 1000 mg, e.g. 30 to 1000 mg, and dosage forms suitable for oral administration comprise from about 1.25 mg to about 500 mg of the compounds admixed with a solid or liquid pharmaceutical carrier or diluent.

A compound of formula I may be administered in free base form. Alternatively any sufficiently basic compound of formula I, e.g. those compounds wherein $R_3$ or $R_4$ contain an amino moiety, may be administered in pharmaceutically acceptable acid addition salt form. Such acid addition salt forms exhibit the same order of activity as the free base forms. The present invention also provides a pharmaceutical composition comprising a compound of formula I in association with a pharmaceutical carrier or diluent. Such compositions may be prepared by conventional techniques to be in conventional forms, for example capsules or tablets.

The compounds of Examples 1, 20, 24, 30–38, 45, 53 and 59 are particularly interesting. The coronary insufficiency, the intermittent claudication, the cerebrovascular insufficiency and the spasmolytic activities are the preferred utilities for compounds of formula I.

In a group of compounds of formula Ia $R_1$ is hydrogen, alkyl, alkenyl, cycloalkyl of 3 to 6 carbon atoms, phenylalkyl, or phenylalkenyl; the phenyl ring being unsubstituted or substituted by one, two or three substituents chosen from one or two halogen radicals, one or two alkyl groups of 1 to 4 carbon atoms, one to three alkoxy groups of 1 to 4 carbon atoms; $R_3^I$ and $R_4^I$, independently, are alkyl, alkenyl, cycloalkyl of 3 to 6 carbon atoms, alkoxy, hydroxyalkoxy of 2 to 6 carbon atoms, alkoxyalkoxy of 3 to 6 carbon atoms, hydroxyalkoxyalkoxy of 4 to 8 carbon atoms, alkenyloxy, or cycloalkyloxy of 3 to 6 carbon atoms, and $R_6$ is other than alkylsulfonyl.

Conveniently $R_1$ is hydrogen, $R_2$ and $R_5$ are each alkyl, especially methyl, $R_3^I$ and $R_4^I$ are each alkoxy, especially ethoxy, $R_6$ is hydrogen or halogen, especially chlorine, especially in the 4 position, the dihydropyridine moiety is in the 4 or 5 position, and X is S.

Alternatively conveniently $R_1$ is hydrogen, $R_2$ and $R_5$ are each alkyl, especially methyl, $R_3^I$ and $R_4^I$ are alkyl or alkoxy, especially methyl, ethyl, tert. butyl, methoxy, ethoxy or tert. butyloxy, $R_6$ is hydrogen or halogen, especially chlorine, or alkoxy, especially methoxy, the dihydropyridine moiety is in the 4 or 5 position and $R_6$ is in the 4, 5 or 7 position.

In one group of compounds of formula I $R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$) or phenylalkyl($C_{7-10}$), $R_3$ and $R_4$, independently are CN, $COR_7$, $COOR_7$ or $S(O)_nR_7$, wherein n is 0, 1 or 2, $R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl, phenylalkyl($C_{7-10}$), a 5- or 6-membered heterocyclic ring containing one heteroatom selected from nitrogen, oxygen or sulphur, or alkyl($C_{1-4}$) substituted by a 5- or 6-membered heterocyclic ring containing one heteroatom selected from nitrogen, oxygen or sulphur, $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)amino, alkanoyl($C_{1-5}$)amino, carbalkoxy($C_{2-4}$), aminocarbonyl, trifluoromethoxy, cyano, sulfamyl, alkyl($C_{1-4}$)sulfamyl or di[alkyl($C_{1-4}$)]sulfamyl, and X is oxygen or sulphur, with the proviso that when $R_1$ is hydrogen, alkyl($C_{1-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenylring being unsubstituted or mono-, di- or tri-substituted independently by halogen, hydroxy, alkyl($C_{1-4}$) or alkoxy($C_{1-4}$), $R_2$ and $R_5$, independently, are hydrogen or alkyl($C_{1-4}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and X is oxygen or sulphur, then at least one of the substituents $R_3$ and $R_4$ is other than $COR_7^I$, wherein $R_7^I$ is alkyl($C_{1-6}$), alkenyl($C_{3-6}$), alkinyl($C_{3-6}$), cycloalkyl($C_{3-7}$), cycloalkylalkyl($C_{4-8}$), and is other than $COOR_7^{II}$, wherein $R_7^{II}$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl($C_{4-8}$).

In another group of compounds of formula I $R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy($C_{1-4}$), $R_2$ and $R_5$, independently, are hydrogen, alkyl($C_{1-6}$) or phenylalkyl($C_{7-10}$), $R_3$ is

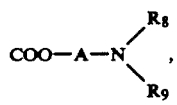

and $R_4$ is CN, $COR_7$, $COOR_7$, $S(O)_nR_7$ or

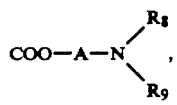

wherein n is 2, $R_7$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl or phenylalkyl($C_{7-10}$), A is alkylene($C_{1-6}$), $R_8$ and $R_9$, independently, are alkyl($C_{1-6}$), alkenyl or alkinyl($C_{3-6}$), cycloalkyl($C_{3-7}$), cycloalkylalkyl($C_{4-8}$), hydroxyalkyl($C_{2-6}$), alkoxyalkyl($C_{3-6}$), hydroxyalkoxyalkyl($C_{4-8}$), aminoalkyl($C_{2-6}$), alkyl($C_{1-4}$)aminoalkyl($C_{2-6}$), phenyl, phenylalkyl($C_{7-10}$), or $R_8$ and $R_9$ together with the nitrogen atom form a 5-, 6- or 7-membered heterocyclic ring, which may contain a further heteromember selected from oxygen, sulphur and a group $=N-R_{10}$, wherein $R_{10}$ is alkyl($C_{1-4}$), and $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro, hydroxy, azido, amino, alkyl($C_{1-4}$)-amino, alkanoyl($C_{1-5}$)amino, carbalkoxy($C_{2-5}$), aminocarbonyl, trifluoromethoxy, cyano or sulfamyl, and X is oxygen or sulphur.

In another group of compounds of formula I $R_1$ is hydrogen, alkyl($C_{1-6}$), alkenyl($C_{3-6}$), alkinyl($C_{3-6}$), cycloalkyl($C_{3-7}$), cycloalkylalkyl($C_{4-8}$), phenylalkyl($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently, are $COR_7^I$ or $COOR_7^{II}$, wherein $R_7^I$ is alkyl($C_{1-6}$), alkenyl($C_{3-6}$), alkinyl($C_{3-6}$), cycloalkyl($C_{3-7}$), cycloalkylalkyl($C_{4-8}$), and $R_7^{II}$ is alkyl($C_{1-6}$), alkenyl($C_{3-6}$), alkinyl($C_{3-6}$), cycloalkyl($C_{3-7}$), cycloalkylalkyl($C_{4-8}$), hydroxyalkyl($C_{2-6}$), alkoxyalkyl($C_{3-6}$) or hydroxyalkoxyalkyl($C_{4-8}$), $R_6$ is hydrogen, halogen, alkyl($C_{1-4}$), alkoxy($C_{1-4}$), alkylthio($C_{1-4}$), alkylsulfonyl($C_{1-4}$), trifluoromethyl, nitro or hydroxy, and X is oxygen or sulphur, with the proviso, that at least one of the substituents $R_2$ and $R_5$ is phenylalkyl($C_{7-10}$), cycloalkyl($C_{3-7}$) or cycloalkylalkyl($C_{4-8}$).

A group of compounds are compounds of formula I, wherein $R_1$ is alkyl($C_{1-6}$), alkoxyalkyl($C_{3-6}$), alkenyl($C_{3-6}$), alkinyl($C_{3-6}$), cycloalkyl($C_{3-7}$), $R_2$ and $R_5$, independently, are hydrogen or alkyl($C_{1-6}$), $R_3$ and $R_4$, independently, are $COOR_7$, wherein $R_7$ is other than phenylalkyl.

These compounds show surprisingly beneficial pharmacological activity than is expected for compounds of this type, e.g. long lasting coronary sufficiency activity in the tests mentioned above and good tolerability.

In another group of formula I $R_1$ is alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl ($C_{7-9}$) or phenylalkenyl($C_{9-12}$), the phenyl ring being unsubstituted or mono-, di- or trisubstituted independently by halogen, hydroxy, alkyl($C_{1-4}$) or alkoxy($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, $COR_7$, $COOR_7$, $S(O)_nR_7$ or

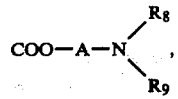

subject to the proviso as defined above, provided that $R_3$ and $R_4$ are not both $COOR_7$, wherein $R_7$ is alkyl($C_{1-6}$).

In another group of compounds of formula I $R_1$ is alkyl($C_{1-6}$), alkenyl($C_{3-6}$), alkinyl($C_{3-6}$), cycloalkyl($C_{3-7}$), $R_2$ and $R_5$, independently, are hydrogen or alkyl($C_{1-6}$), $R_3$ and $R_4$, independently, are CN, $COR_7$, $COOR_7$, $S(O)_nR_7$ or

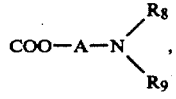

wherein n, $R_7$, A, $R_8$ and $R_9$ and subject to the proviso as defined above and provided that $R_3$ and $R_4$ are not both $COOR_7$, wherein $R_7$ is alkyl($C_{1-6}$).

In a sub-group $R_6$ is alkylsulfonyl($C_{1-4}$), hydroxy, azido, amino, alkyl($C_{1-4}$)amino, di[alkyl($C_{1-4}$)] amino, alkanoyl($C_{1-5}$)amino, aminocarbonyl, tri-fluoromethoxy, sulfamyl, alkyl($C_{1-4}$)sulfamyl or di[alkyl($C_{1-4}$)]sulfamyl.

In another group of compounds of formula I $R_1$ is hydrogen, alkyl($C_{1-6}$), hydroxyalkyl($C_{2-6}$), alkoxyalkyl($C_{3-6}$), alkenyl($C_{3-6}$), alkinyl($C_{3-6}$), cycloalkyl($C_{3-7}$), cycloalkylalkyl($C_{4-8}$), phenylalkyl ($C_{8-9}$) or phenylalkenyl($C_{9-12}$), the phenyl ring being unsubstituted or mono-, di- or trisubstituted independently by halogen, hydroxy, alkyl($C_{1-4}$) or alkoxy ($C_{1-4}$), $R_2$ and $R_5$, independently, are hydrogen, alkyl($C_{1-6}$), phenylalkyl($C_{7-10}$), cycloalkyl($C_{3-7}$) or cycloalkylalkyl($C_{4-8}$), $R_3$ and $R_4$, independently are CN, $COR_7$, $COOR_7$, $S(O)_nR_7$ or

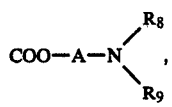

wherein n, $R_7$, A, $R_8$ and $R_9$ and subject to the proviso as defined above, provided that $R_3$ and $R_4$ are not independently $COR_7$, wherein $R_7$ is alkyl($C_{1-6}$), alkenyl($C_{3-6}$), alkinyl($C_{3-6}$) or $COOR_7$, wherein $R_7$ is other than phenyl or phenylalkyl as defined above.

In a first group of compounds $R_1$ is hydrogen.
In a second group of compounds $R_1$ is alkyl.
In a third group of compounds $R_1$ is hydroxyalkyl.
In a fourth group of compounds $R_1$ is alkoxyalkyl.
In a fifth group of compounds $R_1$ is alkenyl.
In a sixth group of compounds $R_1$ is alkinyl.
In a seventh group of compounds $R_1$ is cycloalkyl.
In an eighth group of compounds $R_1$ is cycloalkylalkyl.
In a ninth group of compounds $R_1$ is phenylalkyl.
In a tenth group of compounds $R_1$ is phenylalkenyl.
In an eleventh group of compounds $R_2$ is alkyl.
In a twelfth group of compounds $R_2$ is hydrogen.
In a thirteenth group of compounds $R_2$ is phenylalkyl.
In a fourteenth group of compounds $R_2$ is cycloalkyl.
In a fifteenth group of compounds $R_2$ is cycloalkylalkyl.
In a sixteenth group of compounds $R_5$ is alkyl.
In a seventeenth group of compounds $R_5$ is hydrogen.
In an eighteenth group of compounds $R_5$ is phenylalkyl.
In a nineteenth group of compounds $R_5$ is cycloalkyl.
In a twentieth group of compounds $R_5$ is cycloalkylalkyl.
In a twentyfirst group of compounds $R_5$ is identical to $R_2$.
In a twentysecond group of compounds $R_5$ is a different radical type from $R_2$.
In a twentythird group of compounds $R_3$ is identical to $R_4$.
In a twentyfourth group of compounds $R_3$ is a different radical type from $R_4$.
In a twentyfifth group of compounds $R_3{}^I$ is a different radical type from $R_4{}^I$.
In a twentysixth group of compounds $R_3$ independently is $COR_7$.
In a twentyseventh group of compounds $R_3$ independently is $COOR_7$.
In a twentyeighth group of compounds $R_3$ independently is $SR_7$.
In a twentyninth group of compounds $R_3$ independently is $SOR_7$.

In a thirtieth group of compounds $R_3$ independently is $SO_2R_7$.

In a thirtyfirst group of compounds $R_3$ independently is

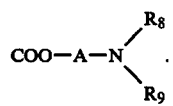

In a thirtysecond group of compounds $R_4$ is $COR_7$.
In a thirtythird group of compounds $R_4$ is $COOR_7$.
In a thirtyfourth group of compounds $R_4$ is $SR_7$.
In a thirtyfifth group of compounds $R_4$ is $SOR_7$.
In a thirtysixth group of compounds $R_4$ is $SO_2R_7$.
In a thirtyseventh group of compounds $R_4$ is $COO-A-NR_8R_4$.
In a thirtyeighth group of compounds $R_7$ is alkyl.
In a thirtyninth group of compounds $R_7$ is alkenyl.
In a fortieth group of compounds $R_7$ is alkinyl.
In a fortyfirst group of compounds $R_7$ is cycloalkyl.
In a fortysecond group of compounds $R_7$ is cycloalkyl.
In a fortythird group of compounds $R_7$ is cycloalkylalkyl.
In a fortyfourth group of compounds $R_7$ is hydroxyalkyl.
In a fortyfifth group of compounds $R_7$ is alkoxyalkyl.
In a fortysixth group of compounds $R_7$ is hydroxyalkoxyalkyl.
In a fortyseventh group of compounds $R_7$ is aminoalkyl.
In a fortyeighth group of compounds $R_7$ is alkylaminoalkyl.
In a fortyninth group of compounds $R_7$ is di[alkyl]aminoalkyl.
In a fiftieth group of compounds $R_7$ is phenyl.
In a fiftyfirst group of compounds $R_7$ is phenylalkyl.
In a fiftysecond group of compounds $R_7$ is a heterocyclic ring.
In a fiftythird group of compounds $R_7$ is an alkyl group substituted by a heterocyclic ring.
In a fiftyfourth group of compounds A is ethylene.
In a fiftyfifth group of compounds X is oxygen.
In a fiftysixth group of compounds X is sulphur.

Any of the above groups may be combined to produce e.g. groups wherein the dihydropyridine substituents in positions 3 and 5, and/or 2 and 6 are identical, different or of a different type (e.g. are grouped in separate groups above).

What we claim is:
1. A compound having the formula

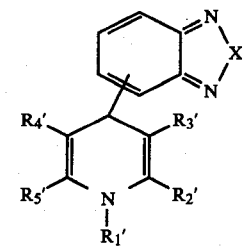

wherein
$R_1'$ is hydrogen or $C_{1-6}$ alkyl;

$R_2'$ and $R_5'$, independently, are hydrogen or $C_{1-6}$ alkyl;

$R_3'$ and $R_4'$, independently, are $COOR_7'$ or

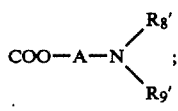

each $R_7'$, independently, is $C_{1-6}$ alkyl, $C_{3-7}$-cycloalkyl, $C_{7-10}$ phenylalkyl or $C_{3-6}$ alkoxyalkyl;

A is $C_{1-6}$ alkylene;

each $R_8'$ and $R_9'$, independently, is $C_{1-6}$ alkyl or $C_{7-10}$ phenylalkyl; and X is oxygen or sulphur, or a pharmaceutically acceptable acid addition salt of a basic compound of the above formula.

2. A compound of claim 1 wherein $R_1'$ is hydrogen.

3. A compound according to claim 1 wherein $R_1'$ is hydrogen, $R_2'$ and $R_5'$ are $C_{1-6}$ alkyl, $R_3'$ and $R_4'$ are $COOR_7'$ where $R_7'$ is $C_{1-6}$alkyl and X is sulphur.

4. A compound according to claim 3 where $R_2'$ and $R_5'$ are methyl and $R_7'$ is methyl, ethyl or t-butyl.

5. A compound according to claim 4 where $R_7'$ is ethyl.

6. The compound of claim 1 which is 4-(2,1,3-benzoxadiazol-4-yl)-2,6-dimethyl-1,4-dihydro-pyridine-3,5-dicarboxylic acid diethyl ester.

7. The compound of claim 1 which is 4-(2,1,3-benzothiadiazol-4-yl)-2,6-dimethyl-1,4-dihydro-pyridine-3,5-dicarboxylic acid dimethyl ester.

8. The compound of claim 1 which is 4-(2,1,3-benzoxadiazol-4-yl)-2,6-dimethyl-1,4-dihydro-3-methoxycarbonylpyridine-5-carboxylic acid isobutyl ester.

9. The compound of claim 1 which is 4-(2,1,3-benzoxadiazol-4-yl)-2,6-dimethyl-1,4-dihydro-3-isopropyloxycarbonyl-pyridine-5-carboxylic acid methyl ester.

10. The compound of claim 1 which is 4-(2,1,3-benzoxadiazol-4-yl)-2,6-dimethyl-1,4-dihydro-3-isopropyloxyethoxycarbonyl-pyridine-5-carboxylic acid methyl ester.

11. The compound of claim 1 which is 4-(2,1,3-benzoxadiazol-4-yl)-2,6-dimethyl-1,4-dihydro-3-ethoxyethoxycarbonyl-pyridine-5-carboxylic acid methyl ester.

12. The compound of claim 1 which is 4-(2,1,3-benzoxadiazol-4-yl)-2,6-dimethyl-1,4-dihydro-3-cyclopentyloxycarbonyl-pyridine-5-carboxylic acid methyl ester.

13. The compound of claim 1 which is 4-(2,1,3-benzoxadiazol-4-yl)-2,6-dimethyl-1,4-dihydro-3-N-benzyl-N-methylamino ethoxycarbonyl-pyridine-5-carboxylic acid ethyl ester, or a pharmaceutically acceptable acid addition salt thereof.

14. The compound of claim 1 which is 4-(2,1,3-benzoxadiazol-4-yl)-2,6-dimethyl-1,4-dihydro-3-methoxycarbonyl-pyridine-5-carboxylic acid benzyl ester.

15. The compound of claim 1 which is 4-(2,1,3-benzothiadiazole-4-yl)-2,6-dimethyl-1,4-dihydro-3-isobutyloxycarbonyl-pyridine-5-carboxylic acid ethyl ester.

16. The compound of claim 1 which is 4-(2,1,3-benzoxadiazole-4-yl)-2,6-dimethyl-1,4-dihydro-3-isobutyloxycarbonyl-pyridine-5-carboxylic acid ethyl ester.

17. The compound of claim 1 which is 4-(2,1,3-benzoxadiazole-4-yl)-2,6-dimethyl-1,4-dihydro-3-ethoxyethoxycarbonyl-pyridine-5-carboxylic acid ethyl ester.

18. The compound of claim 1 which is 4-(2,1,3-benzothiadiazole-4-yl)-2,6-dimethyl-1,4-dihydro-3-ethoxyethoxycarbonyl-pyridine-5-carboxylic acid ethyl ester.

19. The compound of claim 1 which is 4-(2,1,3-benzoxadiazole-4-yl)-2,6-dimethyl-1,4-dihydro-3-methoxyethoxycarbonyl-pyridine-5-carboxylic acid methyl ester.

20. The compound of claim 1 which is 4-(2,1,3-benzoxadiazole-4-yl)-2,6-dimethyl-1,4-dihydro-3-methoxyethoxycarbonyl-pyridine-5-carboxylic acid isopropyl ester.

21. The compound of claim 1 which is 4-(2,1,3-benzoxadiazole-4-yl)-2,6-dimethyl-1,4-dihydro-3-methoxycarbonyl-pyridine-5-carboxylic acid ethyl ester.

22. The compound of claim 1 which is 4-(2,1,3-benzoxadiazole-4-yl)-1-propyl-2,6-dimethyl-1,4-dihydro-pyridine-3,5-dicarboxylic acid diethyl ester.

23. The compound of claim 1 which is 4-(2,1,3-benzoxadiazole-4-yl)-2,6-dimethyl-1,4-dihydro-3-N-benzyl-N-methylamino ethoxycarbonyl-pyridine-5-carboxylic acid methyl ester, or a pharmaceutically acceptable acid addition salt thereof.

24. A pharmaceutical composition useful in treating coronary insufficiency comprising a pharmaceutically acceptable carrier or diluent and a therapeutically effective amount of a compound of claim 1, or a pharmaceutically acceptable acid addition salt thereof.

25. A pharmaceutical composition useful in treating intermittent claudication comprising a pharmaceutically acceptable carrier or diluent and a therapeutically effective amount of a compound of claim 1, or a pharmaceutically acceptable acid addition salt thereof.

26. A pharmaceutical composition useful in treating cerebrovascular accidents comprising a pharmaceutically acceptable carrier or diluent and a therapeutically effective amount of a compound of claim 1, or a pharmaceutically acceptable acid addition salt thereof.

27. A pharmaceutical composition useful in treating muscular spasms comprising a pharmaceutically acceptable carrier or diluent and a therapeutically effective amount of a compound of claim 1, or a pharmaceutically acceptable acid addition salt thereof.

28. A pharmaceutical composition useful in treating hypertension comprising a pharmaceutically acceptable carrier or diluent and a therapeutically effective amount of a compound of claim 1, or a pharmaceutically acceptable acid addition salt thereof.

29. The compound of claim 1 which is 4-(2,1,3-benzoxadiazole-4-yl)-2,6-dimethyl-1,4-dihydro-3-phenethyloxycarbonyl-pyridine-5-carboxylic acid methyl ester.

30. A method of treating coronary insufficiency comprising administering to an animal in need of such treatment a therapeutically effective amount of a compound of claim 1, or a pharmaceutically acceptable acid addition salt thereof.

31. A method of treating intermittent claudication comprising administering to an animal in need of such treatment a therapeutically effective amount of a compound of claim 1, or a pharmaceutically acceptable acid addition salt thereof.

32. A method of treating cerebrovascular accidents comprising administering to an animal in need of such treatment a therapeutically effective amount of a compound of claim 1, or a pharmaceutically acceptable acid addition salt thereof.

33. A method of treating muscular spasms comprising administering to an animal in need of such treatment a therapeutically effective amount of a compound of claim 1, or a pharmaceutically acceptable acid addition salt thereof.

34. A method of treating hypertension comprising administering to an animal in need of such treatment a therapeutically effective amount of a compound of claim 1, or a pharmaceutically acceptable acid addition salt thereof.

* * * * *

UNITED STATES PATENT AND TRADEMARK OFFICE

CERTIFICATE EXTENDING PATENT TERM
UNDER 35 U.S.C. 156

Patent No.    : 4,466,972

Dated         : August 21, 1984

Inventor(s)   : Peter Neumann

Patent Owner  : Sandoz Pharmaceuticals Corporation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 U.S.C. 156(b).

I have caused the seal of the Patent and Trademark Office to be affixed this 30th day of December 1991.

Harry F. Manbeck, Jr.
Assistant Secretary and Commissioner
  of Patents and Trademarks